| United States Patent [19] | [11] Patent Number: 5,439,792 |
|---|---|
| Blake et al. | [45] Date of Patent: Aug. 8, 1995 |

[54] CYSTEINE THIOL-PROTECTED PEPTIDES FOR USE IN IMMUNOASSAYS

[75] Inventors: James Blake; Carol-Ann Cole, both of Seattle; Patrick F. Coleman, Edmonds; Nobuo Monji, Seattle; John P. Montana, Montlake Terrace, all of Wash.

[73] Assignee: Genetic Systems Corporation, Redmond, Wash.

[21] Appl. No.: 140,696

[22] Filed: Oct. 21, 1993

Related U.S. Application Data

[63] Continuation of Ser. No. 532,429, Jun. 4, 1990, abandoned, which is a continuation-in-part of Ser. No. 360,513, Jun. 2, 1989, abandoned.

[51] Int. Cl.$^6$ ............................................. C12Q 1/00
[52] U.S. Cl. ........................................ 435/5; 435/7.92; 435/974; 436/518; 436/531; 530/317; 530/324; 530/334; 530/336; 530/345; 530/402; 530/403; 530/404
[58] Field of Search .................... 435/5, 7.92, 974; 530/324–329, 334, 336, 345, 317, 402, 403, 404; 436/578, 531, 176, 811

[56] References Cited

U.S. PATENT DOCUMENTS

| 4,111,924 | 9/1978 | Fujino et al. ................... 530/326 |
| 4,499,080 | 2/1985 | Duflot et al. .................... 530/326 |
| 4,629,783 | 12/1986 | Cosand ............................ 530/324 |
| 4,689,398 | 8/1987 | Wu et al. . | |

FOREIGN PATENT DOCUMENTS

| 247557 | 12/1987 | European Pat. Off. . |
| 371817 | 6/1990 | European Pat. Off. . |
| 8706005 | 10/1987 | WIPO . |

OTHER PUBLICATIONS

Veber et al., *J. Am. Chem. Soc.* 94:5456–5461 (1972).
Young et al., *Chem. Abstracts* 95:169719 (1981).
Bernatowicz et al., *Proc. 9th Am. Peptide Symposium* (1987).
Brady et al., *Proc. of 10th Am. Peptide Symposium* (1988).
Storey et al, "Studies on Polypeptides. LI. Application S-Ethylcarbamoylcysteine to the Synthesis of a Protected Heptatetracontapeptide Related to the Primary Sequence of Ribonuclease T1", J. Am. Chem. Soc., 94 (17): 6170–6178 (1972).
Kiso et al, "A New Thiol Protecting Trimethylacetamidomethyl Group. Synthesis of a New Porcine Brain Natriuretic Peptide using the S-Trimethylacetamidomethyl-Cysteine", Tetrahedron Lett., 30 (15): 1979–1982 (1989).
Albericio et al, "Use of the Npys thiol protection in solid phase peptide synthesis. Application to direct peptide-protein conjugation through cysteine residues", Chem. Ab., 112(5):34141t (1990). Abstract of Int. J. Pept. Protein Res. 34(2): 124–8 (1989).

*Primary Examiner*—Hazel F. Sidberry
*Assistant Examiner*—Jeffrey Stucker
*Attorney, Agent, or Firm*—Townsend and Townsend Khourie and Crew

[57] ABSTRACT

Peptides immunoreactive with antibodies to native proteins, and which have at least two cysteine residues that contribute to mimicking an epitope of the protein, are prepared with the cysteine thiol groups protected. When deprotected, the peptides have enhanced immunoreactivity. The peptides are particularly useful for detecting antibodies or antigens associated with retroviruses, including the clinically important lymphotropic retroviruses HIV-1, HIV-2, HTLV-I, and HTLV-II.

10 Claims, No Drawings

CYSTEINE THIOL-PROTECTED PEPTIDES FOR USE IN IMMUNOASSAYS

This is a continuation of application Ser. No. 07/532,429, filed Jun. 4, 1990, now abandoned, which is a continuation-in-part of application Ser. No. 07/360,513, filed Jun. 2, 1989, now abandoned.

FIELD OF THE INVENTION

The subject invention relates to peptide compositions which mimic epitopes for use in immunoassays and, more particularly, to improved peptide compositions having enhanced epitope presentation and enhanced specific immunoreactivity with antibodies produced in response to native proteins.

BACKGROUND OF THE INVENTION

Currently individuals with antibodies reactive with human immunodeficiency virus (HIV) are determined by immunoassays of the conventional sandwich ELISA format. These assays are comprised of an immobilized viral lysate that is contacted with blood or serum suspected of containing HIV antibodies. While the existing commercial tests appear to have significantly diminished the transmission of HIV via blood products, viral lysate-based tests have several significant disadvantages. These disadvantages include, but are not limited to, the need to grow and handle large quantities of live infectious virus; the possibility that live virus might be incorporated into test materials; the variable nature of the resulting lysate; and the substantial number of false positive and false negative results which necessitate additional combinatory testing, such as by Western blot.

In commonly owned U.S. Pat. No. 4,629,783 to Cosand, incorporated herein by reference, several synthetic peptides are disclosed which mimic immunologically reactive viral proteins epitopes. Among them, a peptide comprising a sequence of 26 amino acids of gp41, designated peptide 39, was found to be reactive with all known HIV-1 positive sera tested and was not reactive with any negative sample tested. Subsequently, several groups have recognized the importance of the peptide 39 region defined by Cosand as containing a dominant antigenic determinant. See Wang, J. J. G. et al. *Proc. Natl. Acad. Sci.* 83:6159 (1986), Shoeman, R. L. et al. *Analyt. Biochem.* 161:370 (1987), Gnann, J. W. et al. *J. Virol.* 61:2639 (1987), and Gnann, J. W. et al. *J. Infect. Dis.* 156:261 (1987).

Synthetic peptides offer significant advantages over viral lysates. Advantages include, but are not limited to, specificity, purity, ease of production, etc. Potential disadvantages include the need to use more than one peptide to detect all viral strains; and peptides being inherently small in size, loss of immunological reactivity upon immobilization on a solid phase.

Small peptides used as immobilized antigens in immunological assays are generally synthesized by solid phase methods, wherein each amino acid which comprises the peptide is added sequentially in a protected form while the growing peptide chain is immobilized on an insoluble resin support. During the synthetic process side chains of certain amino acids comprising the growing chain are protected, blocked by a variety of chemical groups which remain until the completed peptide is removed from the insoluble resin support, usually by reaction with concentrated hydrofluoric or trifluroacetic acid. During cleavage the majority of the protective groups are removed and the completed peptide is purified by any of a variety of methods well known in the art.

Crude or purified peptide is then immobilized onto a solid phase by a variety of methods, including direct conjugation, conjugation to a soluble non-immunologically reactive protein or other inert molecule, or by direct adsorption onto a solid phase. U.S. Pat. No. 4,629,783 discloses examples of several of these methods.

Peptides which mimic epitopes from the gp36 protein of HIV-2, a glycoprotein believed to be comparable in retroviral function to gp41 of HIV-1, are disclosed in co-owned U.S. patent applications U.S. Ser. No. 030,403 and U.S. Ser. No. 035,408, filed Mar. 25, 1987 and Apr. 7, 1987, respectively, herein incorporated by reference. Among these, a peptide designated 41-2-1, comprised of 26 amino acids encoded within a region similar to that of peptide 39 in HIV-1, was found to be reactive with all known HIV-2 positive sera tested and was not reactive above appropriate cut-off levels with negative samples which were tested. A shortened version of peptide 41-2-1, designated 41-2-3, comprising amino acids residues from the carboxyl end of peptide 41-2-1, was also found to be reactive with the HIV-2 sera and in some cases performed better than peptide 41-2-1.

Peptides 39, 41-2-1 and 41-2-3 each contain within their amino acid sequence two cysteine residues. The presence of cysteine residues within a peptide sequence allows for the formation of inter- and intra-molecular disulfide bonds during purification, immobilization, and upon long term storage of a deprotected peptide. Therefore, such peptide compositions are usually immobilized on a solid phase as a mixture of a variety of oxidative forms, including monomer, dimer and polymers of various sizes. Precautions are generally not taken to control the oxidative form of peptides immobilized on a solid phase. Rosen, J. I. et al. (W087/06005) recognized that certain peptides derived from the highly antigenic region of HIV1, identified by Cosand, supra, which contained more than one cysteine residue were immobilized as a mixture of various oxidative forms and suggested that the oxidative form of a peptide, particularly polymers, may be of importance to the reactivity of certain peptides. Rosen et al. disclose that in some cases the cyclic form of certain peptides is less efficient at binding to solid surfaces than polymeric forms. The variety of oxidative forms of the peptides may be a source of variability in sensitive immunoassay and this may also influence the results based on those assays.

Accordingly, there exists a significant need in the art for peptide compositions with improved reactivity, and which provide as few false-negative and false-positive results as possible. The present invention fulfills these and other needs.

SUMMARY OF THE INVENTION

Improved peptide compositions useful in the detection of HIV viruses or antibody to HIV viruses are provided. Methods are also provided for the preparation of improved peptide compositions which allow for control of the oxidative form of peptides comprising said composition prior to and following immobilization on a solid phase as an antigen in immunoassay methods. Control of the oxidative form provides for peptide compositions with improved immunological reactivity as measured by specificity and sensitivity. Peptides are synthesized using standard solid phase peptide synthesis methods with the exception that a chemically reversible protection means resistant to the highly acidic cleavage conditions is substituted for commonly used S-benzyl blocking of cysteine thiol groups. Chemically reversible protection may be include, for example, ethylcarbamoyl, acetamidomethyl, 3-nitro-2-pyridinesulfinyl, diphenyl-4-pyridyl-methyl, and the like.

An alternate embodiment exists when reversible protection of cysteine thiol groups is provided after the assembly of the amino acid sequence. Reduction of the peptide composition prior to protection of the peptide is necessary to insure no disulfide bonds remain prior to protection. Also, cysteine thiol protection may be removed prior to immobilization wherein deprotection and oxidation of the peptide are carried out in solution prior to immobilization of the oxidized peptide composition to a solid phase. Conditions for oxidation are selected such that the formation of intra-molecular disulfide bonding is favored, i.e., very dilute and neutral to weakly alkaline conditions.

In certain embodiments of the invention the peptides generally are comprised of the amino acid sequence:

Y—Arg—Ile—Leu—Ala—Val—Glu—Arg—Tyr—Leu—Lys—
Asp—Gln—Gln—Leu—Leu—Gly—Ile—Trp—Gly—Cys*—
Ser—Gly—Lys—Leu—Ile—Cys*—X;    (I)

Y—Arg—Val—Thr—Ala—Ile—Glu—Lys—Tyr—Leu—Gln—
Asp—Gln—Ala—Arg—Leu—Asn—Ser—Trp—Gly—Cys*—
Ala—Phe—Arg—Gln—Val—Cys*—X; or    (II)

Y—Gln—Asp—Gln—Ala—Arg—Leu—Asn—Ser—Trp—Gly—
Cys*—Ala—Phe—Arg—Gln—Val—Cys*—X    (III)

wherein X is OH or $NH_2$, Y comprises additional amino acids added to enhance the reactivity of the peptides and Cys* is a cysteine residue comprised of a thiol group protected by chemically reversible means. A particularly preferred embodiment is where Y is the sequence Cys-Gly-Gly.

A wide variety of immunoassay protocols may use peptide compositions, which peptides may be in solution or immobilized on a solid phase. Various solid phases may be used including latexes (microparticulates) of silica, cellulose, fluorocarbon polymers, polyacrylamide and polystyrene. Solid phases comprising, e.g., silica, cellulose, fluorocarbon polymers, nylon, polyacrylamide and polystyrene may also be used. Immobilization to the solid phase may be either by adsorption or by covalent bonding.

One immunoassay protocol disclosed in the present invention for determining the presence of antibodies to HIV viruses or antigens of HIV viruses in a body fluid, generally comprise the steps of (a) contacting, under conditions which permit immobilization, a solid phase and a composition of at least one peptide comprising the amino acid sequence:

Y—Arg—Ile—Leu—Ala—Val—Glu—Arg—Tyr—Leu—Lys—
Asp—Gln—Gln—Leu—Leu—Gly—Ile—Trp—Gly—Cys*—
Ser—Gly—Lys—Leu—Ile—Cys*—X;    (I)

Y—Arg—Val—Thr—Ala—Ile—Glu—Lys—Tyr—Leu—Gln—
Asp—Gln—Ala—Arg—Leu—Asn—Ser—Trp—Gly—Cys*—
Ala—Phe—Arg—Gln—Val—Cys*—X; or    (II)

Y—Gln—Asp—Gln—Ala—Arg—Leu—Asn—Ser—Trp—Gly—
Cys*—Ala—Phe—Arg—Gln—Val—Cys*—X    (III)

wherein X is OH or $NH_2$, Y comprises additional amino acids added to enhance the reactivity of the peptides and Cys* is a cysteine residue comprising a thiol group protected by chemically reversible means; (b) removing the chemically reversible protection means from the cysteine thiol groups of the immobilized peptide; (c) incubating the immobilized peptide under conditions conducive to disulfide bond formation; (d) contacting under conditions which permit immunospecific binding a body fluid with the immobilized peptide to form a reaction mixture; (e) detecting whether immunospecific binding has occurred between the immobilized peptide and an antibody component of the body fluid in which the detection of immunospecific binding indicates the presence of antibodies to the HIV viruses in the body fluid.

A second immunoassay format comprises the steps of (a) removing the chemically reversible protection of the cysteine thiol groups; (b) incubating the deprotected peptide under conditions conducive to intra-molecular disulfide bond formation to form a peptide composition; (c) immobilizing the peptide composition on a solid phase; (d) contacting under conditions which permit immunospecific binding a body fluid with the immobilized peptide composition to form a reaction mixture; and (e) detecting whether immunospecific binding has occurred between the immobilized peptide composition and an antibody component of the body fluid in which the detection of immunospecific binding indicates the presence of antibodies to the HIV viruses in the body fluid.

Immunospecific binding may be detected by removing unbound components from reaction products formed in the immunoreaction mixture, adding a labeled antibody to the immunoreaction mixture, the labeled antibody being capable of immunospecifically binding to a component of the reaction product and the label providing a detectable signal. Unbound components may be removed from the reaction mixture by filtration.

Other aspects of the invention will become evident upon reference to the following detailed description and the appended claims.

DESCRIPTION OF THE SPECIFIC EMBODIMENTS

The present invention relates to improved peptide compositions for use in immunoassay methods for the quantitation and/or detection of antibodies or antigens. In certain embodiments the peptides are used in the detection of viral antigens or antibodies thereto, and more particularly the antigens or antibodies associated with retroviruses, such as HIV-1 and HIV-2 and the related family of lentiviruses. Other exemplary peptides prepared in accordance with the present invention mimic epitopic regions of HTLV-I and HTLV-II.

Peptides may be identified which are capable of binding to antibodies elicited by a protein which is introduced to a foreign host. In several instances Cys residues comprise a portion of the peptide epitope(s) which recognizes and binds the antibodies. Protection of the Cys residues during the synthesis of the peptides hinders the development of oxidative forms of the peptides and provides improved peptide immunological reactivity, as measured by, e.g., increased sensitivity and/or specificity.

Peptide compositions of the subject invention have cysteine residues within said sequence chemically modified so as to be reversibly protected from reaction, e.g., oxidation. Thus a peptide useful in the present invention will generally have at least two Cys residues which contribute to the conformation of the peptide capable of binding antibodies engendered by the native protein. Generally at least two of the Cys residues will be capable of forming intra-molecular disulfide bonds. To form the intra-molecular bonds the Cys residues are separated by at least one amino acid residue, typically at least two, and more usually from about three up to about 15 or more residues. In certain preferred embodiments the Cys residues are separated by about five to eight residues. By forming intra-chain disulfide bonds the vicinal Cys residues present a loop, or cyclic peptide region which may be important in enhanced immunoreactivity.

Peptides of the subject invention may be prepared in a wide variety of ways. The peptides generally range from about six up to about 50 amino acid residues, more typically from about six up to about 35 amino acids. Because of their relatively short length they may be synthesized in solution or on a solid support in accordance with conventional techniques. See, for example, Stewart and Young, *Solid Phase Peptide Synthesis*, 2nd edition, Pierce Chemical Company, 1984; and Tam et al., 1983, *J. Am. Chem. Soc.* 105:6442, which are incorporated herein by reference.

Alternatively, hybrid DNA technology may be employed for expression of the desired peptide in transformed eukaryotic or prokaryotic host cells. See, for example, Maniatis et al., *Molecular Cloning, A Laboratory Manual*, Cold Spring Harbor Press, New York 1982, incorporated herein by reference. Of course, it should be understood that by peptide is meant a sequence of at least about six amino acids, typically ten or more, up to 200 amino acids or more, including entire proteins. The expressed peptide may then be isolated and protected as herein described.

Reversible chemical protection of the cysteine thiol side chain of the subject peptides may be carried out during the assembly of the peptide sequence by chemical synthesis of the peptide composition. When a subject peptide composition is assembled by standard solid phase techniques, a chemically reversible protection means is selected for resistance to the conditions used during the amino acid addition cycles and to the high concentrations of acid used to cleave the peptide from the resin solid phase. Among the several thiol-protecting groups available, the choice for a particular synthesis will likely depend on the structure of the peptide being synthesized and the nature of other protecting or blocking groups being synthesized, as well as the particular reagent chosen for cleavage of the peptide from the resin. Protection means suitable for use in the present invention include, for example, but are not limited to, acetamidomethyl (Stewart and Young, supra), 3-nitro-2-pyridinesulfinyl (Matsueda, et al. 1986, *Int. J. Peptide Res.* 28.:167, Ridge, R. J. et al. 1986, *Int. J. Peptide Res.* 19:490), and diphenyl-4-pyridylmethyl (Coyle, S. et al., 1976, *J. Chem. Soc. Chem. Comm.* pg. 980). A particularly preferred protection is S-(N-ethylcarbamoyl). See, St. Gutmann (*Helv. Chim Acta.* (1966) 49:83) and Storey H. T. et al. (*J. Amer. Chem. Soc.* (1972) 94:6170). Each of the foregoing articles is incorporated herein by reference.

Alternatively, the cysteine thiol groups may be reversibly protected after assembly of the amino acid sequence. In this embodiment the peptide, which may be purified or otherwise enriched in cyclic or polymeric forms, is reduced prior to protection of the peptide to ensure few if any disulfide bonds remain.

The peptides which are thiol-protected are deprotected for use in an immunoassay. The peptide may be used in solution, either free or bound to a carrier, or adsorbed to a solid phase. Cysteine thiol protection may be removed prior to immobilization, if the peptide is to be attached to a solid phase, wherein deprotection and oxidation of the peptide are carried out in solution. Means for deprotection will correspond to a large extent to the particular protecting group used and are well known by those skilled in the arts. Alternatively, deprotection and oxidation may be performed during or subsequent to immobilization. Conditions for oxidation are selected such that the formation of intra-molecular disulfide bonding is favored, i.e., very dilute and neutral to weakly alkaline conditions.

For the detection and/or quantitation of antibodies to HIV, particularly HIV-1, an exemplary peptide capable of mimicking the HIV-1 glycoprotein, gp41, includes the following peptide sequence, where oligopeptides of at least about seven amino acids and less than about 50 will be included within the sequence:

(I)

Y—Arg—Ile—Leu—Ala—Val—Glu—Arg—Tyr—Leu—Lys—
Asp—Gln—Gln—Leu—Leu—Gly—Ile—Trp—Gly—Cys*—
Ser—Gly—Lys—Leu—Ile—Cys*—X;

wherein X is OH or $NH_2$, Y comprises optionally present amino acids added to enhance the reactivity of the peptides and Cys* is a cysteine residue comprising a thiol group protected by chemically reversible means.

For the detection and/or quantitation of antibodies to HIV-2, exemplary peptides capable of mimicking the HIV-2 glycoprotein, gp36, includes the following peptide sequences, where oligopeptides of at least about seven amino acids and less than about 50 will be included within the sequence:

(II)

Y—Arg—Val—Thr—Ala—Ile—Glu—Lys—Tyr—Leu—Gln—
Asp—Gln—Ala—Arg—Leu—Asn—Ser—Trp—Gly—Cys*—
Ala—Phe—Arg—Gln—Val—Cys*—X; or (III)

Y—Gln—Asp—Gln—Ala—Arg—Leu—Asn—Ser—Trp—Gly—
Cys*—Ala—Phe—Arg—Gln—Val—Cys*—X wherein X is OH or $NH_2$, Y comprises optionally present amino acids added to enhance the reactivity of the peptides and Cys* is a cysteine residue comprising a thiol group protected by chemically reversible means.

For the detection and/or quantitation of antibodies to HTLV-I and HTLV-II, exemplary peptides capable of mimicking the HTLV-I and -II transmembrane glycoproteins, both designated gp21, include the following peptide sequences, where oligopeptides of at least about seven amino acids and less than about 50 will be included within the sequences:

IV (HTLV-I)

Y—Gln—Asn—Arg—Arg—Gly—Leu—Asp—Leu—Leu—Phe—Trp—Glu—Gln—Gly—Gly—Leu—Cys*—Lys—Ala—Leu—Gln—Glu—Gln—Cys*—X; and

V (HTLV-II)

Y—Gln—Asn—Arg—Arg—Gly—Leu—Asp—Leu—Leu—Phe—Trp—Glu—Gln—Gly—Gly—Leu—Cys*—Lys—Ala—Ile—Gln—Glu—Gln—Cys*—X;

wherein X is OH or $NH_2$, Y comprises optionally present amino acids added to enhance the reactivity of the peptides and Cys* is a cysteine residue comprising a thiol group protected by chemically reversible means.

It should be understood that the peptide compositions of the present invention need not be identical to any particular protein or retroviral sequence, such as an HIV polypeptide sequence, so long as the subject compositions are able to mimic an epitope and thus provide for immunological competition to some extent with the native protein, e.g., gp41 glycoprotein of at least one strain of HIV-1 or the native gp36 glycoprotein of at least one strain of HIV-2.

For example, the peptides of interest may be modified by introducing conservative or nonconservative substitutions in the peptides, usually fewer than 20 number percent, more usually fewer than 10 number percent of the amino acids being exchanged. It may be desirable to vary one or more particular amino acids to more effectively mimic the differing epitopes of the native protein, such as the different retroviral strains, for example.

Therefore, the subject polypeptides may be subject to various changes, such as insertions, deletions and substitutions either conservative or nonconservative where such changes might provide for certain advantages in their use. By conservative substitutions is intended combinations such as gly, ala; val, ile, leu; asp, glu; asn, gln; ser, thr; lys, arg; and phe, tyr. Usually, the sequence will not differ by more than 20% from the sequence of at least one strain on HIV except where additional amino acids may be added to either terminus to provide for an "arm" by which the subject peptides may be, for example, conveniently immobilized.

In addition, the peptide sequence may differ from the natural sequence in the modification of the terminal $NH_2$ by acylation, e.g., acetylation, or thioglycolic acid amidation, terminal carboxy amidation, e.g., ammonia, methylamine etc. In some instances, these modifications may provide sites for linking to a support or other molecule.

As mentioned above, amino acid arms may be provided at the C- and/or N-terminus of the peptide or oligopeptide. If present, the arms will usually be at least one amino acid and may be 50 or more amino acids, more often 1 to 10 amino acids, and preferably less than 5 amino acids for ease of synthesis. The arms may serve a variety of purposes, such as spacers, to attach peptides to a carrier, to immobilize peptides to a solid phase, etc. To provide useful functionalities for linking to a carrier, solid phase or to form higher-ordered structures, such as dimers, trimers, or other multimers, amino acids such as tyrosine, cysteine, aspartic acid, or the like, may be introduced at provided at the C- and/or N-terminus of the arm or peptide. To enhance epitope presentation, of particular interest is the presence of from 1 to 10 amino acids at the C- and/or N-terminus, more preferably 1 to 5 amino acids, and most preferably about 1 to 3. Particularly preferred embodiments of certain peptides described herein are obtained when 3 amino acids are added as an arm, generally at the N-terminus, with the N-terminal residue of the arm preferably Cys. In exemplary embodiments the spacer residues between the peptide and the terminal functional group are Gly. Thus a particularly preferred peptide has an arm comprising Cys-Gly-Gly, where the Cys is the N- or C-terminal residue. A terminal Cys residue may also be linked through a disulfide linkage to a dithio- or thio-functionalized support or a thioether linkage to an activated olefin support.

Peptide sequences of particular interest for detecting antibodies to HIV-1 are derived from the sequence of Peptide 39 as defined by Cosand, supra. Peptide 39GC, is comprised of the 26 amino acids of Peptide 39, above, wherein Y is comprised of the sequence Cys-Gly-Gly- and X is comprised of —$NH_2$. The peptide therefore is comprised of the amino acid sequence:

Peptide 39GC

Cys—Gly—Gly—Arg—Ile—Leu—Ala—Val—Glu—Arg—Tyr—Leu—Lys—Asp—Gln—Gln—Leu—Leu—Gly—Ile—Trp—Gly—Cys*—Ser—Gly—Lys—Leu—Ile—Cys*—$NH_2$ wherein Cys* are cysteine residues protected by chemically reversible means.

Similarly, peptide sequences of particular interest for detecting antibodies to HIV-2 are derived from the sequence of Peptide 41-2-1, wherein Y is comprised of the sequence Cys-Gly-Gly- and X is comprised of —$NH_2$. The peptide therefore is represented by the amino acid sequence:

Peptide 41-2-1GC

Cys—Gly—Gly—Arg—Val—Thr—Ala—Ile—Glu—Lys—Tyr—Leu—Gln—Asp—Gln—Ala—Arg—Leu—Asn—Ser—Trp—Gly—Cys*—Ala—Phe—Arg—Gln—Val—Cys*—$NH_2$ wherein Cys* are cysteine residues protected by chemically reversible means.

Peptide 41-2-3GC, is comprised of the sequence of 41-2-3, above, wherein Y is the sequence Cys-Gly-Gly and X is $NH_2$ and is represented by the amino acid sequence:

Peptide 41-2-3GC

Cys—Gly—Gly—Gln—Asp—Gln—Ala—Arg—Leu—Asn—Ser—Trp—Gly—Cys*—Ala—Phe—Arg—Gln—Val—Cys*—$NH_2$ wherein Cys* are cysteine residues protected by chemically reversible means.

Peptide sequences of particular interest for detecting antibodies to HTLV-I are derived from the gp21 sequence of Peptide IV. In a preferred embodiment, peptide 121-1GC1, Y is comprised of the sequence Cys-Gly-Gly- and X is comprised of —$NH_2$. The peptide therefore is represented by the amino acid sequence:

121-1GC1

Cys—Gly—Gly—Gln—Asn—Arg—Arg—Gly—Leu—Asp—
Leu—Leu—Phe—Trp—Glu—Gln—Gly—Gly—Leu—Cys*—
Lys—Ala—Leu—Gln—Glu—Gln—Cys*—NH$_2$, wherein Cys* are cysteine residues protected by chemically reversible means.

Peptide sequences of particular interest for detecting antibodies to HTLV-II are derived from the gp21 sequence of Peptide V. In a preferred embodiment, peptide 221-1GC1, Y is comprised of the sequence Cys-Gly-Gly- and X is comprised of —NH$_2$. The peptide therefore is represented by the amino acid sequence:

221-1GC1

Cys—Gly—Gly—Gln—Asn—Arg—Arg—Gly—Leu—Asp—
Leu—Leu—Phe—Trp—Glu—Gln—Gly—Gly—Leu—Cys*—
Lys—Ala—Ile—Gln—Glu—Gln—Cys*—NH$_2$;

wherein Cys* are cysteine residues protected by chemically reversible means. It should be understood that due to substantial sequence homology between the HTLV-I and -II peptides described herein, some cross-reactivity between the peptides is to be expected.

The format for the immunoassay in which peptides prepared according to the present invention are employed is dependent on whether antibody or antigen is to be determined. Immunoassay formats designed to detect antibody or antigen are well known in the art. Prior to or at the time of reacting the sample with the peptide, however, the chemical protection of the peptide is removed and the deprotected peptide is incubated under conditions conducive to disulfide bond formation. In assay formats where the peptide is immobilized to a solid phase the peptide cysteine residues may be deprotected in solution under conditions conducive to the formation of intramolecular disulfide bonds prior to or after immobilization.

The peptide compositions may be used unlabeled or labeled depending upon their application. (By label is intended a molecule which provides, directly or indirectly, a detectable signal.) Various labels may be employed, such as radionuclides, enzymes, fluorescers, chemiluminescers, enzyme substrates, cofactors or inhibitors, particles, e.g., magnetic particles, combinations of ligands and receptors, e.g., avidin and biotin, or the like. In addition, the polypeptides may be modified in a variety of ways for binding to a surface, e.g., microtiter plates, glass or latex beads, tubes, filters, chromatographic surfaces, e.g., paper, cellulose, silica gel, or the like. The particular manner in which peptides may be joined to another compound or solid phase surface is conventional and finds ample illustration in the literature. See, for example, U.S. Pat. Nos. 4,371,515; 4,487,715; and patents cited therein. Reagents such as p-maleimidobenzoic acid, p-methyldithiobenzoic acid, maleic acid anhydride, succinic acid anhydride, glutaraldehyde, hetero-bifunctional cross-linkers, and the like are commonly used for such purposes.

Various assay protocols may be employed for detecting the presence of either antibodies to retroviral proteins or retroviral proteins themselves. The peptide may be used as the labeled reagent, where the label allows for a detectable signal. Alternatively, the peptide may be immobilized either directly or indirectly on a surface, where antibody to the peptide in the sample will become bound to the peptide on the surface. The presence of human antibody bound to the peptide can then be detected by employing a xenogeneic antibody specific for human immunoglobulin, normally both human IgG and IgM, or a labeled protein specific for immune complexes, e.g., Rf factor or S. aureus protein A.

Various heterogeneous protocols may be employed, either competitive or non-competitive. Peptide may be bound to a surface or support and labeled antibody allowed to compete with antibody in the sample for the limited amount of bound peptide. The amount of label bound to the support would be related to the amount of competitive antibody in the sample.

Antibody could be bound to the support and the sample combined with labeled peptide. After contact of the reaction mixture with the bound antibody, the amount of label bound to the support would relate to the amount of cognate antibody in the sample.

Xenogeneic anti-human antibody, e.g., antibodies to the Fc of IgG and IgM (immunoglobulins), could be bound to a support. The sample would be contacted with the immunoglobulins and labeled peptide, whereby the amount of labeled peptide bound to the support would be indicative of the presence of the cognate antibodies.

Illustrative of an assay technique is the use of immunoconcentration, e.g., filtration, where the subject peptide composition or conjugates thereof are adsorbed to a solid phase, e.g., latex beads, either covalently or noncovalently. The sample, a biological fluid sample, e.g., saliva, urine, cerebral spinal fluid, blood, plasma, or serum, may be pretreated by dilution into an assay medium, which will usually be an aqueous buffered medium employing one of a variety of buffers, such as phosphate, Tris, or the like, is combined with the antigen coated latex beads in a container, with a filter membrane, and a sufficient time allowed for complex formation between the peptide(s) and any cognate antibodies in the sample. The supernatant is allowed to pass through the filter and the filter upon which the coated beads are immobilized is washed to remove nonspecifically bound proteins.

A labeled specific binding protein which specifically binds to the complex is employed for detection. To the immunoreactive membrane may be added xenogeneic antisera to human immunoglobulin, particularly anti-(human IgG and IgM) in an appropriately buffered medium. The xenogeneic antisera will normally be labeled with a detectable label, e.g., enzyme or radionuclide. Instead of antisera, proteins specific for the immune complex may be employed, e.g., S. aureus protein A. The label may then be detected. For example, with an enzyme, after removal of non-specifically bound enzyme label, a developer solution is added. The developer solution will contain an enzyme substrate and possibly enzyme cofactors, chromogens, etc., which, upon reaction, provide a colored or fluorescent product which may be detected colorometrically or fluorimetrically, respectively.

The following examples are offered by way of illustration and not by way of limitation.

EXAMPLE I

Thiol-Deprotected Peptides Detect Antibodies to HIV-1 and HIV-2

Synthesis of Peptides

Derivatives of Peptide 39 were assembled by the sequential coupling of t-butyloxycarbonyl-protected amino acids onto 0.40 mmol p-methylbenzhydrylamine resin (Applied Biosystems Inc., Foster City, Calif.). Amino acid side chain protection was by standard benzyl based groups. Tryptophan was protected by the formyl moiety. When chemically reversible protection of a cysteine residue was desired protection was provided by using ethylcarbamoyl protection and coupling was achieved using standard hydroxybenzotriazole ester chemistry as used for glutamine or asparagine.

N-t-butyloxycarbonyl-S-ethyl-carbamoylcysteine was prepared as described by St. Gutmann, and Storey et al. supra. Briefly, 15.3 ml of trifluroacetic acid was added dropwise into a mixture of 24.2 g L-cysteine (free base) and 200 ml of dimethylformamide (DMF) at 0° C. with constant stirring. Ethyl isocyanate (17.8 ml) was then added dropwise and the mixture stirred at room temperature for 18 hrs. The resultant mixture was evaporated under vacuum and the residue dissolved in 180 ml of water. Two portions of ether (100 ml) cooled to 0° C. was used to wash the aqueous solution and the pH was adjusted to 7.0 by the addition of sodium hydroxide. Absolute ethanol (550 ml) was added, and the product was allowed to crystallize overnight at 4° C. Washing the crystalline solid with cold 20% ethanol/water and ether after filtration yielded 18.9 g of S-ethylcarbamoylcysteine.

To make the N-t-butyloxycarbonyl derivative, 23 g of solid di-t-butyl dicarbonate was slowly added to a vigorously stirring mixture of 18.9 g S-ethylcarbamoylcysteine, 180 ml dimethyl sulfoxide and 16.4 ml diisopropylethylamine. The mixture was stirred for 2 hrs at room temperature before 400 ml ice water plus 100 ml of saturated sodium chloride was added. Hydrochloric acid was added to adjust the pH of the mixture to 2.0 and the aqueous mixture was washed with two, 200 ml portions of ethyl acetate. The organic extracts were combined and evaporated under vacuum. The residue was recrystallized from ethyl acetate/hexane followed by recrystallization from 20% ethanol/water. A 19.4 g yield of N-t-butyloxycarbonyl-S-ethylcarbamoylcysteine was obtained.

The final product was shown to be homogeneous by thin layer chromatography on silica gel with a chloroform/acetic acid (15:1) solvent; Rf 0.25. The melting point of the product was 144°–146° C., similar to that previously reported to be 139°–140° C. (Storey supra).

Completed peptides were deprotected and cleaved from the resin by the standard high HF procedure or the low-high HF procedure of Tam et al. (*J. Amer. Chem. Soc.* 105:6442, 1983). Peptide was extracted from the resin in 50% acetic acid and subjected to gel chromatography in 20% acetic acid on G-25 Sephadex. Fractions containing peptide were pooled and lyophilized.

Immunological Reactivity

Peptide 39 and its analogues were tested for immunological reactivity by a test tube assay wherein the peptides were immobilized by adsorption or covalent bonding onto latex beads.

Adsorption of peptide 39GC and deprotected peptide 39GC onto latex beads was carried out by first washing the beads (5 mg, IDC, Interfacial Dynamics Corporation, Portland Ore., 1 μm diameter) with distilled water and resuspending in 0.5 ml of 0.1M HEPES, pH 7.4, with vigorous mixing. Diluted peptide from a 4 mg/ml 6M GuHCl stock solution was added to the washed beads (25–200 μg peptide) to a final volume of 550 μl. The mixture was vigorously stirred for 30 sec. followed by less vigorous mixing overnight. Following overnight incubation 500 μl of distilled water was added and the beads were collected by centrifugation. The beads were washed with 1 ml of distilled water twice before being suspended in 100 μl of distilled water followed by the addition of 100 μl 0.5N NaOH with immediate mixing to deprotect the cysteine residues of the adsorbed peptide. Deprotection was stopped with the addition of 1 ml 0.25N HEPES, pH 7.4.

Air oxidation of the peptide/bead solution was carried out overnight at room temperature. Potassium ferricyanide was added to the peptide/bead solution to complete the oxidation. The tube was centrifuged and the beads were washed three times with 1 ml of distilled water. Peptide/bead complex can be used immediately or stored as aqueous suspensions at 4° C. for periods of up to 6 months without significant loss of reactivity.

Peptide 39, wherein X is —OH, Y is —NH$_2$ and cysteine thiol groups are not EC protected, was adsorbed to latex beads by adding 0.1 ml of a 2 mg/ml peptide stock solution of peptide 39 in 6M guanidine-HCl to washed latex beads (prepared as above) which had been resuspended in 0.9 ml of 0.2M Tris, pH 8.0. The peptide latex bead suspension was incubated overnight at 45° C. in a water bath. After incubation the beads were collected by centrifugation and washed once in 0.01M PBS, pH 7.0.

Peptide coated beads may be blocked, if necessary, to aid in the prevention of non-specific binding by the addition of 20 μl of a 0.84% [w/v] suspension of coated beads to 1 ml of 1% bovine serum albumin (BSA) and mixing vigorously. Beads were collected by centrifugation and the supernatant removed. Wash steps were repeated twice subsequently.

Serum or plasma to be tested was diluted 1:80 in sample dilution buffer (2.5%[w/v] nonfat dry milk, 15 ppm Kathon CG, 0.01% antifoam A in 0.01M sodium phosphate, pH 7.2, 0.15M sodium chloride) and 100 μl was added to the blocked peptide/latex bead conjugate with mixing by vortex. The sample was incubated with the peptide/latex bead conjugate for 15 min. at room temperature before adding 0.9 ml of wash solution (0.05% Tween 20 in Tris-saline, 1 mM magnesium chloride), vortexing and centrifuging to collect the peptide/bead conjugate. Peptide/bead conjugate was washed again and collected by centrifugation and 100 μl of a 1/100 dilution of anti human-IgG,A and M-alkaline phosphatase conjugate in dilution buffer was added for 15 min. at room temperature. The peptide/bead conjugate was washed again as above.

Immunological reactivity of the peptides was detected indirectly by the alkaline phosphatase activity. Enzyme buffer (0.8 ml, 0.1M Tris-HCl/0.1M NaCl/5 mM MgCl$_2$, pH 9.5) was added, followed by 100 μl of substrate (9 mg p-nitrophenyl phosphate in enzyme buffer). Substrate was incubated for 15 min. at 37° C. and the reaction was stopped by the addition of 100 μl of 3N sodium hydroxide. The beads were pelleted by centrifugation and the supernatant was measured for absorbance in a spectrophotometer at 405 nm. Peptides 39GC and 39GC deprotected showed substantial improvement over Peptide 39 in this assay format.

Alternatively, peptides were immobilized covalently onto latex beads through the carboxyl terminus. Carboxyl terminal conjugation was carried out with a peptide 39 analog, designated 39-I, which is comprised of the following sequence:

Arg—Ile—Leu—Ala—Val—Glu—Arg—Tyr—Leu—Lys—

Asp—Gln—Gln—Leu—Leu—Gly—Ile—Trp—Gly—Cys*—

Ser—Gly—Lys—Leu—Ile—Cys*—Thr—Gly—SH,

Cysteine residues were ethylcarbamoyl protected and the peptide was synthesized as described above. Completed peptide was cleaved from the solid phase using 90% hydrofluoric acid/10% anisole at 0° C., in vacuo, with stirring. Hydrofluoric acid was evaporated and the residue was washed with ethyl acetate prior to dissolving the crude peptide in 6M Gu-HCL/0.4M potassium phosphate. Crude peptide was citraconylated by the procedure of Blake et al. (*Int. J. Peptide Res.* 1981, 17:273, *Proc. Natl. Acad. Sci. USA* 1981, 78:4055, both incorporated herein by reference) followed by gel filtration in ammonium bicarbonate buffer. The resultant peptide, 39-IX, was comprised of an amino terminus and lysine residues which had been citraconylated, formyltryptophan, ethylcarbamoyl-cysteines and C-terminal thioglycine residue.

Peptide 39-IX was conjugated to the free amino groups of pentalysines conjugated to carboxylated latex beads (Seradyne, 1.1 μm diameter, 0.01 meq/g) via carbodiimide activation. An aliquot of bead suspension (0.3 ml) was centrifuged to collect the beads. Beads were washed once with distilled water, collected and suspended in a solution of H-Lys-Lys-Lys-Lys-Lys-amide in water. The pH was adjusted to between 5.0 and 5.5 prior to the addition of 1-ethyl-3-(3-dimethylaminopropyl)-carbodiimide (EDC). After standing overnight the beads were collected and washed with distilled water as above.

Half of the resultant beads were treated with 27 μg/mg beads of peptide 39-IX in an aqueous solution of silver nitrate and 0.1M N-hydroxysuccinimide at pH 7.4 for 2 hrs. at room temperature. The beads were washed with 0.2M sodium cyanide and stored in 15% aqueous acetic acid overnight to remove the citraconyl groups. Ethylcarbamoyl and formyl protecting groups were removed by a brief treatment with 0.2N sodium hydroxide. Cysteine residues were allowed to air oxidize overnight, followed by reaction with potassium ferricyanide to ensure complete oxidation.

The remaining pentalysine conjugated latex beads were treated in an identical fashion as above, except no silver nitrate was added. The resultant beads served as a blank for comparison.

Peptide 39 derivatives were also covalently immobilized through the amino terminus to carboxy modified latex beads (Polysciences) via carbodiimide activation. Eight milligrams of latex beads were placed in a microfuge tube and 0.5 ml of distilled water was added. The beads were collected by centrifugation and the supernatant removed. Activation was carried out by adding 0.5 ml of 0.2M EDC (38.2 mg/ml) and 0.1M N-hydroxysuccinimide (22 mg/ml) and allowing the reaction to proceed for 90 min. at room temperature with rotary mixing. Activated beads were collected as above and all but about 50 μl of supernatant removed. The pellet was dispersed and 250 μl of 1M HEPES, pH 7.5, containing various concentrations of peptide 39, were added (190–760 μg). Peptide was allowed to react with the activated beads overnight at room temperature with rotary mixing. Beads were collected as above and washed with 0.1M HEPES, pH 7.5. Two additional washes were carried out with 1% BSA in Tris-saline(0.1M, pH 7.4) and the peptide/latex beads were resuspended in 0.5 ml of 1% BSA/Tris-saline.

Alternatively N-terminal covalent immobilization was carried out via thioether bond formation. Peptide 39-GC was conjugated to $NH_2$ modified latex beads (Pandex, Mundelein, Ill.). Five milligrams of beads were washed once with distilled water and resuspended in 200 μl of 0.1M HEPES, pH 7.4. N-succinimidyl-4-(N-maleimidomethyl)-cyclohexane-1-carboxylate (SMCC, 100 μl of 1 mg/100 μl in DMF) was added to the bead suspension and allowed to react for 2 hrs. at room temperature with constant mixing. Activated beads were collected as above, washed twice with distilled water, and once with 0.1M HEPES, pH 7.4, containing 5 mM EDTA. A 200 μl suspension of activated beads in HEPES buffer was prepared and 200 μl of peptide 39-GC in 100 μl of 6M GuHCl was added. Conjugation was allowed to proceed overnight at room temperature in a rotator. Peptide conjugated beads were collected as above, washed three times in distilled water and suspended at 0.84% in distilled water. Immunologic cross-reactivity was tested as described above.

Alternative methods of testing immunologic cross-reactivity were also used. In one such method Peptides 39 and 39GC were tested by ELISA as previously described in U.S. Pat. No. 4,629,783. Briefly, stock solutions of peptides 39 and 39-GC were prepared in 6M Gu-HCl. Working dilutions of 20 μl/ml and 6 μl/ml respectively were prepared by dilution of stock solution with 0.05M carbonate/bicarbonate buffer, pH 9.5. Wells of microtiter plates were filled with 100 μl of the working dilution of the peptides and allowed to stand overnight at room temperature. Coating solution was removed and 300 μl of blocking solution supra containing 0.5M ethanolamine was added for 1 hr. at room temperature. Blocking solution was removed and the plates were used immediately or allowed to dry and stored for later use.

Plasma samples were diluted (See Table 1) in sample dilution buffer (above) and 100 μl was added to individual wells. Samples were incubated for 30 min. at 37° C., then removed and the wells were washed six times with 0.15M NaCl, 0.05% Tween 20. One hundred microliters of goat antihuman Ig-horseradish peroxidase conjugate diluted in citrate buffer, pH 7.0, 1% normal goat serum was added to each well for 30 min at 37° C. prior to washing six times as above. The ELISA assay was developed by adding 100 μl/well of substrate solution (80 μl/ml tetramethyl benzidine, 0.0015% hydrogen peroxide in citrate/phosphate buffer, pH 6.0) for 30 min. at room temperature. Reactions were stopped with the addition of 100 μl of 1N $H_2SO_4$ per well, and the ratio of the optical density at 450 nm to 630 nm was determined by an automated ELISA reader. The cutoff value for a positive result was set at 0.225 Absorbance Units above the average absorbance obtained for three known negative samples. The results in Table 1 show that Peptide 39GC was able to give a positive result at a higher dilution than Peptide 39.

In separate experiments the thiol-protected peptide 39GC showed markedly reduced immunoreactivity in assays when compared to thiol-deprotected peptide 39GC. Similar results were observed with the HIV-2 peptide, 41-2-3GC.

TABLE 1

DILUTION PANEL COMPARISON OF PEPTIDE 39 AND PEPTIDE 39GC BY ELISA

| Sample | Diagnosis 39GC/39 | Confirmed Seropositive | PEPTIDE 39GC | PEPTIDE 39 |
|---|---|---|---|---|
| PlasmaO (1:40) | Pos/Pos | Yes | 1.439 | 0.859 |
| PlasmaO (1:80) | Pos/Pos | Yes | 1.010 | 0.547 |
| PlasmaO (1:160) | Pos/Pos | Yes | 0.742 | 0.351 |
| PlasmaO (1:320) | Pos/Neg | Yes | 0.397 | 0.197 |
| PlasmaO (1:640) | Neg/Neg | Yes | 0.279 | 0.128 |
| PlasmaO (1:1280) | Neg/Neg | Yes | 0.165 | 0.078 |
| PlasmaG (1:40) | Pos/Pos | Yes | 0.895 | 0.585 |
| PlasmaG (1:80) | Pos/Neg | Yes | 0.820 | 0.321 |
| PlasmaG (1:160) | Pos/Neg | Yes | 0.575 | 0.241 |
| PlasmaG (1:320) | Neg/Neg | Yes | 0.349 | 0.148 |
| PlasmaG (1:640) | Neg/Neg | Yes | 0.179 | 0.092 |
| PlasmaG (1:1280) | Neg/Neg | Yes | 0.107 | 0.078 |
| Cutoff Value | | | 0.348 | 0.341 |

EXAMPLE II

Membrane Concentration Immunoassay for Antibodies to HIV-1 Using Deprotected Peptides Various known serum and plasma samples were screened for immunologic cross-reactivity using a modified microparticulate assay employing the improved methods and compositions of the present invention. The subject peptide compositions were immobilized onto latex beads and entrapped on a microporous membrane atop an absorbent material for the determination and/or quantitation of antibodies to HIV. Examples of such immunoassay apparatus and methods are the subject of U.S. Pat. Nos. 4,633,901 and 4,727,019, both incorporated herein by reference. The membrane concentration immunoassay involves three incubations comprising a total assay time of 10 minutes. Peptides tested were adsorbed to latex beads by the methods described above.

Each sample was tested on a filtration unit comprising three spots on a 1.2 μm pore size nylon membrane. One spot comprising the test peptide/latex bead preparation, one spot comprising a positive procedural control and the other comprising a negative procedural control.

The peptide/latex bead preparation was suspended in 0.1M Tris buffer, pH 7.2, 0.15M NaCl, 0.01M MgCl$_2$, 10% sucrose, 2% fetal calf serum. Membranes were spotted with a 0.1–0.2% suspension of peptide/bead preparation. Negative procedural control spots were comprised of latex beads coated by adsorption with BSA. While positive procedural control spots were comprised of latex beads coated by adsorption with goat antihuman immunoglobulins.

Serum or plasma samples (40 μl) were diluted 1:10 in dilution buffer (10% heat inactivated normal goat serum, 1% dextran sulfate, 0.2% Tween 20, 2.5% non-fat dry milk, 15 ppm Kathon CG, 0,005% antifoam A, in 20 mM sodium citrate buffer, pH 7.4). Diluted specimen was added to the surface of the membrane and allowed to absorb completely. After waiting 2 min. from the time of specimen addition, 1 ml of wash buffer (0.01M Tris-buffered saline, pH 6.0, 0.05M NaCl, 0.05M MgCl$_2$, 0.1% sodium azide, 10 μl/ml nitro blue tetrazolium, 0.5M potassium thiocyanate) was added and allowed to completely absorb through the membrane. About 0.150 ml (3 drops) of goat anti-human Ig-alkaline phosphatase conjugate diluted in 10 mM phosphate buffered saline, pH 7.4, 0.2% goat gamma globulin, 1% bovine serum albumin, 1 mM MgCl$_2$, 0.1 mM ZnCl$_2$ was added to the membrane and allowed to absorb completely. The membrane was washed twice as above (2 ml) and about 0.150 ml (3 drops) of substrate (1M 2-amino-2-methyl-l-propanol, pH 10.3, 5 mg/ml 3-indoxyl phosphate) was added and allowed to absorb completely. After about 5 min. about 1 ml of 0.5M EDTA, pH 7.4, was passed through the membrane to stop the reaction. After the stop solution was completely absorbed the units were read visually or semi-quantitatively by reflectance.

A result was negative if only the positive control spot showed any sign of color development and the test spot and the negative control spot showed no color development. A positive result was indicated if the test spot showed some level of color development (trace to 4+), the positive control spot shows color development and the negative control spot showed no color development. The test was considered to be invalid if all spots showed any color development, no color development was seen for the positive control, or if the negative control spot showed any color development.

A wide variety of positive, negative, EIA positive/western blot atypical and immune sensitized specimens have been tested with the preferred peptide 39 analog, peptide 39-GC, as the test antigen. Positive specimens showed a gradation of reactivity from 0.5+ to 4+, all valid tests resulting in clearly defined colored spots on a clean white background. The negative control showed no color development and the positive control gave approximately 2+ coloration.

TABLE 2

SUMMARY OF RESULTS OF VARIOUS TYPES OF SAMPLES TESTED BY MEMBRANE IMMUNOCONCENTRATION IMMUNOASSAY WITH PEPTIDE 39-GC AS THE ANTIGEN

| Category | No. Positive/Total No. |
|---|---|
| Normal Blood Bank Donors | 0/1187 |
| Western Blot Neg./LAV-EIA Pos. | 0/79 |
| Western Blot p25 Neg./LAV/EIA Pos. (Atypical 1) | 0/39 |
| Western Blot p25 Pos./LAV-EIA Pos. (Atypical 2) | 0/170 |
| Western Blot Pos./LAV-EIA Pos.(OD<1.5) | 120/120 |
| Western Blot Pos./LAV-EIA Pos.(OD>1.5) | 29/29 |
| Autoimmune Samples[1] | 0/51 |
| Secondary, Atypical Syphillis Sera/HIV Neg. | 0/26 |
| Secondary, Atypical Syphillis Sera/HIV Pos. | 4/4 |
| Problematic HIV-I Seronegative Samples[2] | 0/72 |
| | n = 1777 |

[1] Autoimmune samples included 11 asthma patients, 11 Sjogren's syndrome patients, 7 systemic lupus erythematosus patients, 4 ankylosing spondylitis patients, 3 unknown conditions and 15 assorted syndromes/diseases.
[2] Icteric, lipemic, bacteremic, ascorbic acid and various anticoagulant treated samples.

Various peptide compositions of the subject invention have been tested using some of the assay formats described above. A summary of the results is found in the following tables. In Table 3 results of the comparison of Peptide 39 by ELISA and membrane concentration immunoassay with whole virus ELISA on atypical samples are given. Ten of the eleven atypical samples tested positive by whole virus ELISA and were not confirmed to be positive by Western Blot. All were found to be negative when Peptide 39 was used as the immobilized antigen by both ELISA and membrane concentration immunoassay.

Results of whole virus ELISA with Peptide 39GC by ELISA and membrane concentration immunoassay and Peptide 39 by ELISA on two seroconversion panels are presented in Table 4. Peptide 39GC and peptide 39 gave a positive result earlier than whole virus ELISA. Peptide 39GC gave a positive result earlier than peptide 39 on one of the seroconversion panels.

TABLE 3
ENZYME LINKED IMMUNOASSAY COMPARISON OF PEPTIDE AND WHOLE VIRUS AS ANTIGEN ON WESTERN BLOT ATYPICAL SERUM SAMPLES

| Specimen | Diagnosis LAV/ Peptides | Confirmed Seropositive | LAV ELISA | Peptide 39 ELISA | Peptide 39 MCI[1] |
|---|---|---|---|---|---|
| Y34150 | Pos/Neg | No | 0.526 | 0.063 | Neg |
| Z00132 | Neg/Neg | No | 0.307 | 0.083 | Neg |
| H62111 | Pos/Neg | No | 0.751 | 0.047 | Neg |
| V45719 | Pos/Neg | No | 0.581 | 0.048 | Neg |
| Y49300 | Pos/Neg | No | 0.523 | 0.048 | Neg |
| V44932 | Pos/Neg | No | 0.617 | 0.068 | Neg |
| G16211 | Pos/Neg | No | 0.387 | 0.027 | Neg |
| G15694 | Pos/Neg | No | 0.367 | 0.078 | Neg |
| Y40646 | Pos/Neg | No | 0.655 | 0.057 | Neg |
| H63547 | Pos/Neg | No | 0.901 | 0.092 | Neg |
| Y38248 | Pos/Neg | No | 0.386 | 0.048 | Neg |

[1]Membrane Concentration Immunoassay

TABLE 4
COMPARATIVE RESULTS USING PEPTIDE AS ANTIGEN IN ELISA AND MEMBRANE CONCENTRATION IMMUNOASSAY FORMATS FOR TWO SEROCONVERSION PANELS

| Sample Number | Diagnosis | Confirmed Sero-positive | LAV ELISA | Peptide 39GC | Peptide 39 | MCI 39GC |
|---|---|---|---|---|---|---|
| BBI-1 | Negative | No | 0.067 | 0.347 | 0.128 | — |
| BBI-2 | Negative | No | 0.075 | 0.317 | 0.129 | — |
| BBI-3 | Pos/Neg | Yes | 0.180 | 0.842 | 0.514 | + |
| BBI-4 | Positive | Yes | 0.858 | 1.105 | 0.632 | ++ |
| BBI-5 | Positive | Yes | 1.164 | 1.757 | 1.098 | ++ |
| BBI-6 | Positive | Yes | 1.359 | 2.160 | 1.531 | ++ |
| BBI-7 | Positive | Yes | 1.430 | 1.986 | 1.307 | ++ |
| BBI-8 | Positive | Yes | 1.556 | 2.317 | 1.688 | +++ |
| BBI-9 | Positive | Yes | 1.507 | 2.328 | 2.122 | +++ |
| Cutoff Value | | | 0.291 | 0.384 | 0.341 | |
| BBI-20 | Negative | No | 0.038 | 0.136 | 0.037 | — |
| BBI-21 | Negative | No | 0.055 | 0.158 | 0.053 | — |
| BBI-22 | Pos/Neg | Yes | 0.057 | 0.450 | 0.244 | + |
| BBI-23 | Pos/Neg | Yes | 0.123 | 0.890 | 0.540 | + |
| BBI-24 | Pos/Neg | Yes | 0.127 | 1.064 | 0.636 | + |
| BBI-25 | Pos/Neg | Yes | 0.216 | 0.845 | 0.553 | ++ |
| BBI-26 | Pos/Neg | Yes | 0.259 | 0.852 | 0.445 | ++ |
| BBI-27 | Positive | Yes | 0.335 | 1.104 | 0.590 | ++ |
| BBI-28 | Positive | Yes | 0.431 | 1.177 | 0.769 | ++ |
| BBI-29 | Positive | Yes | 0.718 | 2.085 | 1.566 | ++ |
| BBI-30 | Positive | Yes | 0.837 | 2.214 | 1.871 | +++ |
| BBI-31 | Positive | Yes | 0.798 | 2.207 | 1.812 | +++ |
| BBI-32 | Positive | Yes | 0.920 | 2.263 | 1.925 | +++ |
| BBI-33 | Positive | Yes | 0.833 | 2.277 | 1.961 | +++ |
| BBI-34 | Positive | Yes | 0.728 | 1.622 | 1.363 | +++ |
| BBI-35 | Positive | Yes | 0.902 | 2.198 | 1.861 | +++ |
| BBI-36 | Positive | Yes | 0.881 | 2.265 | 1.959 | +++ |
| BBI-37 | Positive | Yes | 0.953 | 2.105 | 1.530 | +++ |
| Cutoff Value | | | 0.291 | 0.384 | 0.341 | |

EXAMPLE III

Detection of Antibodies to HIV-2 Using Deprotected Peptides

The immunoreactivity of HIV-2 peptides synthesized with protected cysteine thiol groups was determined. HIV-2 peptide 41-2-3 was synthesized as described in Example I, with the Cys groups protected and having an N-terminal Cys-Gly-Gly, yielding peptide 41-2-3GC. EIAs were performed as described above using viral lysates of HIV-1 and HIV-2 and peptides 39GC (HIV-1) and 41-2-3GC. Reactivity was determined for dilutions of two HIV-2 positive sera, F504282, obtained from a patient in New York, and "GOM," provided by the Institut Pasteur. The results, shown in Table 5, demonstrate that the synthetic peptides clearly differentiate between HIV-1 and HIV-2 and provide particularly enhanced specific immunoreactivity when compared to results obtained with the whole virus lysate EIAs.

TABLE 5
Reactivities in EIA of dilutional series prepared from HIV-2 positive specimens

| Dilution | HIV-1 Peptide 39GC | HIV-2 Peptide 41-2-3GC | HIV-1 Lysate | HIV-2 Lysate |
|---|---|---|---|---|
| A* | | | | |
| Neat | 0.075 | 3.000 | ND# | 2.026 |
| 1:5 | 0.049 | 3.000 | 0.494 | 1.808 |
| 1:10 | 0.042 | 3.000 | 0.293§ | 1.687 |
| 1:20 | 0.037 | 3.000 | 0.170 | 1.405 |
| 1:40 | 0.035 | 2.828 | 0.101 | 1.182 |
| 1:80 | 0.033 | 2.107 | 0.072 | 0.876 |
| 1:160 | 0.040 | 1.441 | 0.046 | 0.597 |
| 1:320 | 0.031 | 0.941 | 0.039 | 0.367 |
| 1:640 | 0.031 | 0.588 | 0.034 | 0.171 |
| 1:1280 | 0.039 | 0.302 | ND | ND |
| 1:2560 | 0.030 | 0.180 | ND | ND |
| B* | | | | |
| 1:2 | 0.052 | 3.000 | 0.839 | 2.113 |
| 1:4 | 0.037 | 3.000 | 0.510 | 1.953 |
| 1:8 | 0.040 | 3.000 | 0.317 | 1.703 |
| 1:16 | 0.031 | 3.000 | 0.177 | 1.433 |
| 1:32 | 0.035 | 3.000 | 0.099 | 1.083 |
| 1:64 | 0.074 | 2.524 | 0.060 | 0.736 |
| 1:128 | 0.031 | 2.202 | 0.047 | 0.552 |
| 1:256 | 0.035 | 1.452 | ND | 0.280 |
| 1:512 | 0.040 | 0.811 | ND | 0.176 |
| 1:1024 | 0.037 | 0.571 | ND | 0.114 |

*A is serum from patient F504282, B is serum from patient GOM.
ND = Not Determined.
§Line represents cutoff, values above which are positive and below are considered negative.

The immunoreactivity of unprotected HIV-2 peptide 41-2-3 was compared to the deprotected form having a Cys-Gly-Gly extension at the N-terminus (41-2-3GC), and with an HIV-2 whole virus lysate. The assays were EIAs performed generally as described above with varying dilutions of HIV-2 positive serum specimens. The results for representative sera are shown in Table 6.

TABLE 6
Reactivity of Selected HIV-2 Sera with Deprotected and Unprotected HIV-2 Peptides and HIV-2 Viral Lysate.

| Specimen | Dilution | 41-2-3GC | 41-2-3 | Lysate |
|---|---|---|---|---|
| "GOM" | 1:2 | 3.000 | 2.239 | 2.113 |
| | 1:4 | 3.000 | 1.932 | 1.953 |
| | 1:8 | 3.000 | 1.517 | 1.703 |
| | 1:16 | 3.000 | 1.143 | 1.433 |
| | 1:32 | 3.000 | 0.693 | 1.083 |
| | 1:64 | 2.524 | 0.343§ | 0.736 |
| | 1:128 | 2.202 | 0.228 | 0.552 |
| | 1:256 | 1.452 | 0.092 | 0.280 |
| | 1:512 | 0.811 | 0.069 | 0.176 |
| | 1:1024 | 0.571 | 0.058 | 0.114 |
| "PIN" | 1:2 | 3.000 | 2.082 | 1.336 |
| | 1:4 | 3.000 | 1.695 | 1.035 |
| | 1:8 | 2.596 | 1.154 | 0.834 |
| | 1:16 | 1.940 | 0.607 | 0.711 |
| | 1:32 | 1.209 | 0.369 | 0.387 |
| | 1:64 | 0.582 | 0.182 | 0.188 |
| | 1:128 | 0.368 | 0.123 | 0.147 |
| | 1:256 | 0.186 | 0.091 | 0.087 |
| "SAMB" | 1:2 | 3.000 | 1.535 | 1.047 |
| | 1:4 | 3.000 | 1.089 | 0.968 |
| | 1:8 | 2.854 | 0.659 | 0.708 |

Peptides were synthesized and protected generally according to the procedures outlined in Example I. Assays were performed generally as described in Examples I and II. The results are shown in Table 6.

TABLE 6

HTLV-I Peptides Tested for Reactivity to Antibodies to HTLV-I.

| Peptide§/Sequence | Serum Sample# | | |
|---|---|---|---|
| | 40359 | 0435 | 032EC1 |
| 121-1G1<br>H- QNRRGLDLLFWEQGGLC*KALQEQC*-NH₂ | trace | — | — |
| 121-1GC1<br>H- CGG-QNRRGLDLLFWEQGGLC*KALQEQC*-NH₂ | 3+ | 1+ | — |
| 121-2G1<br>H- GLDLLFWEQGGLC*KALQEQC*-NH₂ | — | — | — |
| 121-2GC1<br>H- CGG-GLDLLFWEQGGLC*KALQEQC*-NH₂ | 3+ | 0.5+ | — |
| 121-3G1<br>H- NRRGLDLLFWEQGGLC* -NH₂ | — | — | — |
| 121-3GC1<br>H- CGG-NRRGLDLLFWEQGGLC*-NH₂ | 3+ | — | — |
| 121-3EG1<br>H- C*GG-NRRGLDLLFWEQGGLC*-NH₂ | ND | — | — |
| 121-1D1<br>H-QNRRGLDLLFWEQGGLCKALQEQC-OH | ND | — | — |

§Coating level for peptides on latex microparticles was 50 μg peptide/5 mg beads/550 μl volume.
Serum samples 40359 and 0435 are HTLV-I EIA positive control sera used undiluted; 032EC1 is HTLV-L EIA Negative control.
*Indicates Cys residue was protected during synthesis using ethylcarbamoyl protection.

Results of assays with peptide 121-1GC1 were compared to those obtained with other HTLV-I/II tests, such as the polymerase chain reaction (PCR), radioimmunoprecipitation (RIP), Western blot (WB), and viral lysate EIAs. The procedure as described in Example II was used for peptide 121-1GC1, except that two drops of samples were used and the conjugate was used at a two-fold higher concentration. The assays were performed with 10 serum samples suspected of containing antibodies to HTLV-I and/or HTLV-II. The PCR assay for HTLV-II was performed generally according to *PCR Technology, Principles and Applications for DNA Amplification*, ed. H. A. Ehrlich, Stockton Press, New York (1989), incorporated herein by reference. The results are shown in Table 7.

TABLE 7

Comparison of Assays for HTLV-I/II with Deprotected Peptide 121-1GC1.

| Sample No. | PCR HTLV-II | EIA HTLV-I | RIP HTLV-L | WB HTLV-L | Status | 121-1GC1 |
|---|---|---|---|---|---|---|
| 89379 | + | + | + | + | + | trace |
| 89365 | + | + | — | vw§ | Ind# | 0.5+ |
| 39266 | + | + | — | vw | Ind | trace |
| 89430 | + | + | — | + | Ind | trace |
| 89433 | + | + | — | — | Ind | 1+ |
| 89442 | — | + | — | Ind | Ind | trace |
| 89232 | + | + | + | + | + | trace |
| 89283 | + | + | + | + | + | 1+ |
| 89359 | + | + | + | + | + | 1+ |
| 88002 | | | | | | — |
| 12-97-854 | | | | | | — |

Coating Level: 80 μg peptide/5 mg bead/550 μl volume
§vw is very weak reaction.
Ind is indeterminant status.

EXAMPLE IV

Detection of Antibodies To HTLV-I Using Deprotected Peptides

A region of HTLV-I transmembrane glycoprotein, gp21, was identified as corresponding to transmembrane regions of HIV-1 and HIV-2 and thus potentially immunodominant. Synthetic peptides were prepared based on the known amino acid sequence of HTLV-I.

In other experiments, screening of the HTLV-I peptide in a variety of forms against a serum panel of suspected HTLV-I/II positive individuals yielded inconclusive results when compared to results obtained by RIP, Western blot, and commercially available HTLV-I EIA assays. Some samples which were purportedly positive by certain of the tests were negative with peptide 121-1GC1. These results may be due to several factors, including the possibility that samples negative by peptide 121-1GC1 and positive by other criteria contained antibodies predominantly reactive with virus core antigens and not with transmembrane glycoprotein antigens.

Although the present invention has been described in some detail by way of illustration and example for purposes of clarity and understanding, it will be obvious that certain changes and modifications may be practiced within the scope of the appended claims.

What is claimed is:

1. A method for preparing a peptide coated solid phase for immunological detection and/or quantitation of antibody to a cyclic viral protein epitope, comprising:
   (a) synthesizing the peptide which comprises an amino acid sequence of 10 to 50 amino acids and having two Cys residues which are separated from each other by at least about three but fewer than twenty non-Cys amino acid residues;
   (b) protecting thiol groups of the cysteine encoded within the peptide sequence by chemically reversible means resistant to highly acidic cleavage to form a protected peptide composition;
   (c) immobilizing the protected peptide composition on a solid phase;
   (d) removing the chemically reversible protection means from the immobilized peptide composition; and
   (e) incubating the immobilized peptide composition under conditions conducive to the formation of disulfide bonds between the Cys residues.

2. The method of claim 1, wherein the peptide sequence is:

Y—Arg—Ile—Leu—Ala—Val—Glu—Arg—Tyr—Leu—Lys—
Asp—Gln—Gln—Leu—Leu—Gly—Ile—Trp—Gly—Cys*—
Ser—Gly—Lys—Leu—Ile—Cys*—X,

Y—Arg—Val—Thr—Ala—Ile—Glu—Lys—Tyr—Leu—Gln—
Asp—Gln—Ala—Arg—Leu—Asn—Ser—Trp—Gly—Cys*—
Ala—Phe—Arg—Gln—Val—Cys*—X,

Y—Gln—Asp—Gln—Ala—Arg—Leu—Asn—Ser—Trp—Gly—
Cys*—Ala—Phe—Arg—Gln—Val—Cys*—X,

Y—Gln—Asn—Arg—Arg—Gly—Leu—Asp—Leu—Leu—Phe—
Trp—Glu—Gln—Gly—Gly—Leu—Cys*—Lys—Ala—Leu—
Gln—Glu—Gln—Cys*—X, or

Y—Gln—Asn—Arg—Arg—Gly—Leu—Asp—Leu—Leu—Phe—
Trp—Glu—Gln—Gly—Gly—Leu—Cys*—Lys—Ala—Leu—
Gln—Glu—Gln—Cys*—X, wherein X is OH or $NH_2$, Y comprises 1-5 amino acids added to enhance presentation of immunological epitopes reactive with antibodies to HIV and Cys* is a cysteine residue comprising a thiol group protected by chemically reversible means resistant to highly acidic cleavage.

3. A method of claim 2, wherein the thiol groups of Cys* are protected by acetamidomethyl, 3-nitro-2-pyridinesulfinyl, diphenyl-4-pyridylmethyl or S-(N-ethylcarbamoyl).

4. The method of claim 3, wherein the thiol groups of Cys* are protected by S-(N-ethylcarbamoyl).

5. A method for the preparation of an antigen coated solid phase for immunological detection and/or quantitation of antibody to a cyclic protein epitope of HIV viruses, comprising:
   (a) synthesizing a peptide which comprises from 10 to 50 amino acids and having two Cys residues which are separated from each other by at least about three but fewer than twenty non-Cys amino acid residues, wherein the cysteine thiol groups are protected by chemically reversible means resistant to highly acidic cleavage to form a protected peptide;
   (b) immobilizing said peptide onto a solid phase to form an antigen coated solid phase; and
   (c) removing said chemically reversible protection means from said protected peptide under conditions conducive to intramolecular disulfide bond formation between the cysteine residues.

6. A method for preparing a peptide coated solid phase for immunological detection and/or quantitation of antibody to an antigenic viral protein, comprising:
   (a) synthesizing the peptide to have one of the following amino acid sequences:

(I)
Y—Arg—Ile—Leu—Ala—Val—Glu—Arg—Tyr—Leu—Lys—
Asp—Gln—Gln—Leu—Leu—Gly—Ile—Trp—Gly—Cys*—
Ser—Gly—Lys—Leu—Ile—Cys*—X;

(II)
Y—Arg—Val—Thr—Ala—Ile—Glu—Lys—Tyr—Leu—Gln—
Asp—Gln—Ala—Arg—Leu—Asn—Ser—Trp—Gly—Cys*—
Ala—Phe—Arg—Gln—Val—Cys*—X; or (III)
Y—Gln—Asp—Gln—Ala—Arg—Leu—Asn—Ser—Trp—Gly—
Cys*—Ala—Phe—Arg—Gln—Val—Cys*—X wherein X is OH or $NH_2$, Y comprises 1-5 amino acids added to enhance presentation of immunological epitopes reactive with antibodies to HIV and Cys* is a cysteine residue comprising a thiol group protected by chemically reversible means resistant to highly acidic cleavage;
   (b) protecting thiol groups of the cysteine encoded within the peptide sequence by chemically reversible means resistant to highly acidic cleavage to form a protected peptide composition;
   (c) immobilizing the protected peptide composition on a solid phase;
   (d) removing the chemically reversible protection means from the immobilized peptide composition; and
   (e) incubating the immobilized peptide composition under conditions conducive to the formation of disulfide bonds between the Cys residues.

7. A method for determining the presence of antibodies to HIV viruses or antigen of HIV viruses in a body fluid, comprising:
   (a) contacting under conditions which permit immobilization, a carrier and a composition containing at least one peptide comprising the amino acid sequence:

(I)

Y—Arg—Ile—Leu—Ala—Val—Glu—Arg—Tyr—Leu—Lys—
Asp—Gln—Gln—Leu—Leu—Gly—Ile—Trp—Gly—Cys*—
Ser—Gly—Lys—Leu—Ile—Cys*—X;

(II)

Y—Arg—Val—Thr—Ala—Ile—Glu—Lys—Tyr—Leu—Gln—
Asp—Gln—Ala—Arg—Leu—Asn—Ser—Trp—Gly—Cys*—
Ala—Phe—Arg—Gln—Val—Cys*—X; or (III)

Y—Gln—Asp—Gln—Ala—Arg—Leu—Asn—Ser—Trp—Gly—
Cys*—Ala—Phe—Arg—Gln—Val—Cys*—X wherein X is OH or $NH_2$, Y comprises 1-5 amino acids added to enhance presentation of immunological epitopes reactive with antibodies to HIV of the peptides and Cys* is a cysteine residue comprising a thiol group protected by chemically reversible means resistant to highly acidic cleavage;

(b) removing the chemically reversible protective means from the cysteine thiol groups of the immobilized peptide;

(c) incubating the immobilized peptide under conditions conducive to disulfide bond formation;

(d) contacting under conditions which permit immunospecific binding the body fluid with the immobilized peptide to form a reaction mixture;

(e) detecting whether immunospecific binding has occurred between the immobilized peptide and an antibody component of the body fluid in which the detection of immunospecific binding indicates the presence of antibodies or antigens of the HIV viruses in the body fluid.

8. A method of claim 7, wherein the thiol groups of Cys* are protected by acetamidomethyl, 3-nitro-2-pyridinesulfinyl, diphenyl-4-pyridylmethyl or S-(N-ethylcarbamoyl).

9. The method of claim 8, wherein the thiol groups of Cys* are protected by S-(N-ethylcarbamoyl).

10. A method as in claim 7, wherein the carrier is a solid phase.

* * * * *